US00PP18781P2

(12) United States Plant Patent
Stemkens

(10) Patent No.: US PP18,781 P2
(45) Date of Patent: Apr. 29, 2008

(54) ***VERBENA* PLANT NAMED 'IPINENA'**

(50) Latin Name: *Verbena×hybrida*
Varietal Denomination: Ipinena

(75) Inventor: Henricus G. W. Stemkens, Hoorn (NL)

(73) Assignee: Syngenta Seeds B.V., Enkhuizen (NL)

( * ) Notice: Subject to any disclaimer, the term of this patent is extended or adjusted under 35 U.S.C. 154(b) by 0 days.

(21) Appl. No.: 11/640,772

(22) Filed: Dec. 18, 2006

(51) Int. Cl.
*A01H 5/00* (2006.01)

(52) U.S. Cl. ..... Plt./308
(58) Field of Classification Search ..... Plt./308
See application file for complete search history.

*Primary Examiner*—Anne Marie Grunberg
*Assistant Examiner*—S. B. McCormick-Ewoldt
(74) *Attorney, Agent, or Firm*—S. Matthew Edwards

(57) ABSTRACT

A new *Verbena* plant particularly distinguished by its deep pink flower, early flowering, and a habit that is very compact and later spreading.

1 Drawing Sheet

Latin name of the genus and species of the plant claimed: *Verbena×hybrida.*
Varietal denomination: 'Ipinena'.

BACKGROUND OF THE NEW PLANT

The present invention comprises a new distinct cultivar of *Verbena,* botanically known as *Verbena×hybrida.*

The new cultivar is originated from the cross of 'B0859-5' as female parent and 'C0776-4' as the male or pollen parent. 'B0859-5' is a rose flowering *Verbena.* 'B0859-5' is not commercially available and is not known by any synonyms. 'B0859-5' has not been patented. 'C0776-4' is a pink flowering *Verbena.* 'C0776-4' is not commercially available and is not known by any synonyms. 'C0776-4 has not been patented.

As a result of this cross the present cultivar was created in 2003 in Enkhuizen, Netherlands and has been repeatedly asexually reproduced by cuttings in Enkhuizen, Netherlands and Sarrians, France over a two year period. The new variety is stable and reproduces true to type in successive generations of asexual reproduction.

This new *Verbena* plant is an annual in most climatical zones in the US, only in zones 6, 7, 8, 9 and 10 it is a perennial plant.

DESCRIPTION OF THE DRAWING

This new *Verbena* plant is illustrated by the accompanying photographic drawing which shows blooms, buds and foliage of the plant in full colour, the colour shown being as true as can be reasonably obtained by conventional photographic procedures.

DESCRIPTION OF THE NEW CULTIVAR

The following detailed descriptions set forth the distinctive characteristics of this new *Verbena.* The data that define these characteristics were collected from asexual reproductions carried out in Enkhuizen, Netherlands. The plant history was taken on 14 week old plants, blossomed under natural light in a greenhouse and grown in a 10.5 cm container. Colour readings were taken in the greenhouse under ambient light.

Color references are primarily to the R.H.S. Colour Chart of The Royal Horticultural Society of London.

TABLE 1

DIFFERENCES BETWEEN THE NEW CULTIVAR 'IPINENA,' ITS PARENTS AND THE MOST RESEMBLING VARIETY

| | 'IPINENA' | 'B0859-5' | 'C0776-4' | 'Tapien salmon' |
|---|---|---|---|---|
| Flower color | Deep pink | Rose | Pink | Salmon |
| Earliness | Mid early | Early | Late | Very Late |

The commercial name of the most resembling variety is 'Tapien salmon'. This variety has commercial name "SUNMAREF TP-SAP' and is patented as U.S. Plant Pat. No. 14,117.

The plant:

*Classification.*—Botanical: *Verbena×hybrida.*
*Parentage.*—Female: A seedling named 'B0859-5' is one of our seedlings from our B-generation of plants. Male: A seedling named 'C0776-4' is one of our seedlings from our C-generation of plants.
*Growth habit.*—Compact, decumbent.
*Plant height.*—8-10 cm.
*Spreading area of plant.*—20-25 cm.
*Branching character.*—Freely branching and lateral branching at every node.
*Number of branches per plant.*—18-20.
*Blooming period.*—From March until November.

The stem:

*Diameter.*—2 mm.
*Length.*—10-13 cm.
*Shape.*—Tetragonal.
*Anthocyanin pigmentation.*—Absent.
*Colour of the stem.*—137B.
*Length of internode.*—18 mm.
*Texture.*—Smooth.
*Pubescence.*—Slightly pubescent.
*Length lateral branches.*—14 cm.

The foliage:

*Phyllotaxis.*—Opposite.
*Shape of blade.*—Lanceolate.

*Texture.*—Upper side: Smooth. Lower side: Smooth.
*Venation.*—Pinnate.
*Leaf margin.*—Double incised.
*Leaf base.*—Obtuse.
*Leaf apex.*—Acute.
*Length.*—14-18 mm.
*Width.*—10-14 mm.
*Depth of incision.*—8-10 mm.
*Number of incisions.*—2-6 per leaf.
*Colour.*—Upper side: 138B. Lower side: 138C.
*Pubescence.*—Slightly pubescent.
*Length of petiole.*—3-4 mm.
*Petiole surface structure.*—Slightly pubescent.
*Petiole diameter.*—1 mm.
*Petiole coloration.*—138B, both surfaces.

The bud:
*Peduncle length.*—18-20 mm.
*Peduncle diameter.*—1 mm.
*Peduncle color.*—143B.
*Bud size.*—Diameter: 2 mm. Length: 4*6 mm.
*Bud shape.*—Elongated and ovate.
*Bud color.*—137C.
*Sepals.*—Color (upper side): 143B. Color (lower side): 143B. Form: Upright. Number: 5, fused. Length: 7-8 mm. Width: 2 mm. Shape: Elongated. Apex: Emarginate. Base: Fused. Margin: Entire.

The flower:
*Flower diameter.*—10-14 mm.
*Flower height.*—12-16 mm.
*Flower tube length.*—10-14 mm.
*Flower throat diameter.*—2 mm.
*Flower throat color.*—156B.
*Inflorescence.*—Corymb.
*Flower.*—Form: Single, salverform; sessile on terminal corymbs.
*Petal colour.*—Upper side: N57B. Lower side: 61C.
*Overlapping of petals.*—Separate.
*No. of petals.*—Gamopetalous, 5 lobed.
*Petal apex.*—Obcordate.
*Petal base.*—Fused.
*Petal margin.*—Entire.
*Petal surface texture.*—Smooth.
*Size of the petal.*—Length: 5-7 mm. Width: 4-5 mm.
*Inflorescence.*—Length: 18-24 mm. Diameter: 18-25 mm.
*Calyx length.*—8 to 10 mm.
*Calyx diameter.*—3-4 mm.
*Anthocyanin pigmentation of calyx limb.*—Present, Color: 61B.
*Color of the calyx.*—143B.
*No. of flowers per inflorescence.*—20-30.
*Fragrance.*—No fragrance.
*Bloom time of one inflorescence.*—New florets continue to open in one corymb over a period of 14 days.
*Lastingness of one flower.*—2-4 days.

Reproductive organs:
*Androecium.*—Stamens quantity: 4. Anther shape: Ovoid. Anther length: 1 mm. Anther color: 144C. Pollen amount: No pollen.
*Gynoecium.*—Pistils quantity: 1. Pistil length: 1-1.5 cm. Stigma shape: Bi-lobed. Stigma color: 144C. Style length: 1.9 cm. Style color: 144C. Ovary color: 144C.

The fruit and the seed: No fruit development or seed set has been observed to date.

Roots:
*Type of roots.*—Fibrous, color 155C. Roots start to grow on every part of the stem that contacts the soil, so not only at the nodes.

Physiological and ecological characteristics:
*Disease/pest resistance.*—Plants of the new *Verbena* have been noted to be resistant to especially powdery mildew.
*Temperature tolerance.*—Plants of the new *Verbena* have been observed to tolerate temperatures from −8-35 degrees C.

What is claimed is:

1. A new and distinct variety of *Verbena* plant, substantially as illustrated and described herein.

* * * * *

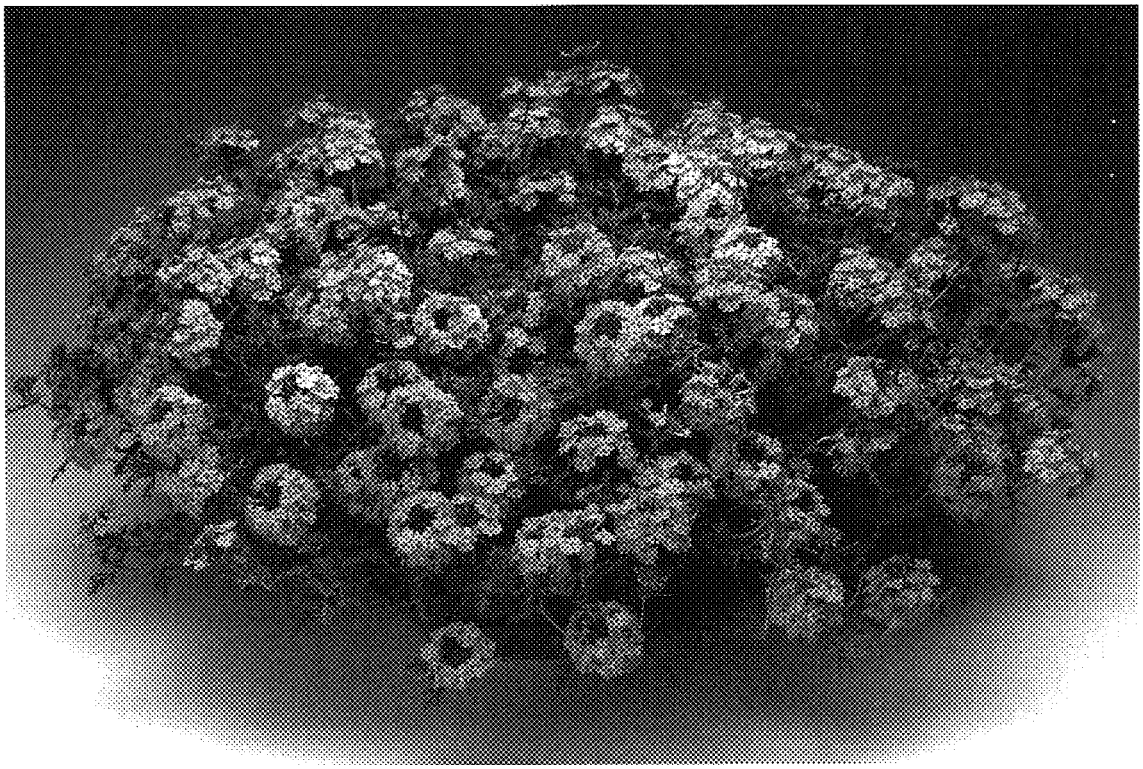

UNITED STATES PATENT AND TRADEMARK OFFICE

CERTIFICATE OF CORRECTION

PATENT NO. : PP 18,781 P2
APPLICATION NO. : 11/640772
DATED : April 29, 2008
INVENTOR(S) : Henricus G.W. Stemkens It is certified that error appears in the above-identified patent and that said Letters Patent is hereby corrected as shown below:

At column 1, line 9, delete “is” before “originated”

At column 3, line 20 under “Bud size” and following “Length:”, delete “4*6 mm” and insert therefor --4-6 mm--

Signed and Sealed this

Eighth Day of July, 2008

JON W. DUDAS
*Director of the United States Patent and Trademark Office*